United States Patent
Wrobel

(10) Patent No.: US 10,962,520 B2
(45) Date of Patent: Mar. 30, 2021

(54) METHOD AND DEVICE FOR DETERMINING AND/OR MONITORING THE BREAKDOWN VOLTAGE OF A TRANSFORMER OIL

(71) Applicant: PASSERRO GMBH, Leipzig (DE)

(72) Inventor: Matthias Wrobel, Munich (DE)

(73) Assignee: PASSERRO GMBH, Leipzig (DE)

(*) Notice: Subject to any disclaimer, the term of this patent is extended or adjusted under 35 U.S.C. 154(b) by 153 days.

(21) Appl. No.: 16/331,773

(22) PCT Filed: Sep. 6, 2017

(86) PCT No.: PCT/EP2017/072287
§ 371 (c)(1),
(2) Date: Mar. 8, 2019

(87) PCT Pub. No.: WO2018/050500
PCT Pub. Date: Mar. 22, 2018

(65) Prior Publication Data
US 2019/0277805 A1 Sep. 12, 2019

(30) Foreign Application Priority Data
Sep. 13, 2016 (DE) .................... 10 2016 117 188.3

(51) Int. Cl.
G01N 33/28 (2006.01)
G01H 3/04 (2006.01)
(Continued)

(52) U.S. Cl.
CPC ............ *G01N 33/28* (2013.01); *G01H 3/04* (2013.01); *G01H 15/00* (2013.01);
(Continued)

(58) Field of Classification Search
CPC .... G01N 33/28; G01N 29/348; G01N 29/024; G01N 29/032; G01N 29/346;
(Continued)

(56) References Cited

U.S. PATENT DOCUMENTS

2016/0169839 A1* 6/2016 Gottlieb ............... G01N 29/024
367/7
2018/0266996 A1* 9/2018 Fokow ............... G01N 33/2847

FOREIGN PATENT DOCUMENTS

| DE | 19706486 A1 | 8/1998 |
| DE | 102013005003 A1 | 9/2014 |
| DE | 102014104963 A1 | 10/2014 |

OTHER PUBLICATIONS

PCT International Search Report, PCT/EP2017/072287, dated Jan. 2, 2018, 4 pages.
(Continued)

*Primary Examiner* — David Z Huang
(74) *Attorney, Agent, or Firm* — Quarles & Brady LLP

(57) ABSTRACT

The disclosure relates to a method for determining and/or monitoring the breakdown voltage of a transformer oil, comprising the steps of
a) performing an acoustic impedance measurement of the transformer oil, the impedance of a medium partially or entirely disposed in the transformer oil and capable of naturally vibrating and/or transmitting vibrations to the transformer oil is determined in at least one frequency band of defined frequency width; and
b) calculating a resonator quality factor for the frequency band based on the determination performed in step a); and
c) calculating an acoustic disbalance of the transformer oil based on the calculation performed in step b); and
d) ascertaining the breakdown voltage of the transformer oil based on the calculation performed in step c).

(Continued)

Figure 1:
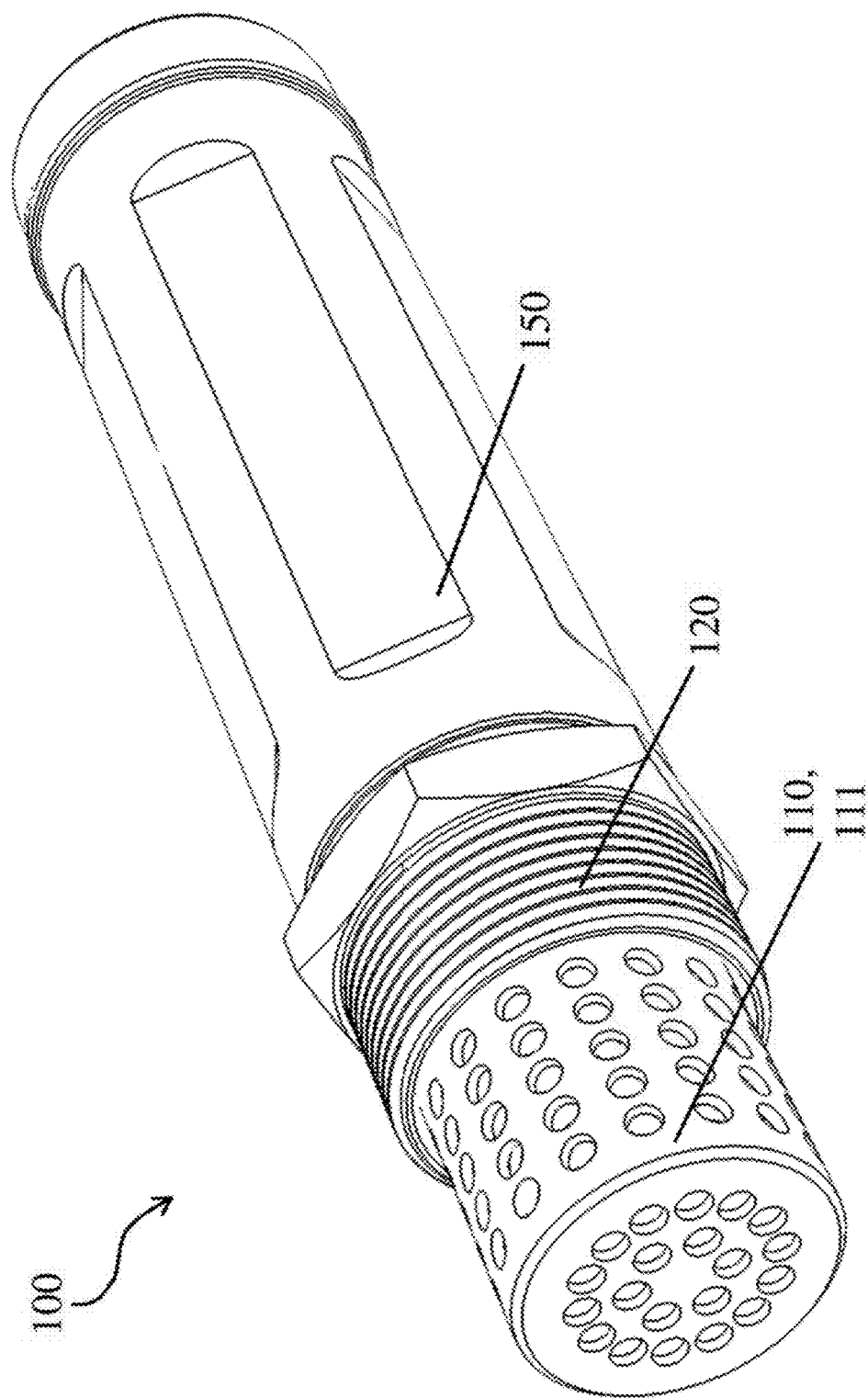

Furthermore, the disclosure relates to a device (100, 200) for determining and/or monitoring the breakdown voltage of a transformer oil.

14 Claims, 12 Drawing Sheets

(51) Int. Cl.
| | | |
|---|---|---|
| *G01N 29/024* | (2006.01) | |
| *G01N 29/032* | (2006.01) | |
| *G01N 29/34* | (2006.01) | |
| *G01N 29/44* | (2006.01) | |
| *G01H 15/00* | (2006.01) | |

(52) U.S. Cl.
CPC ......... *G01N 29/024* (2013.01); *G01N 29/032* (2013.01); *G01N 29/346* (2013.01); *G01N 29/348* (2013.01); *G01N 29/4436* (2013.01); *G01N 2291/011* (2013.01); *G01N 2291/015* (2013.01); *G01N 2291/0226* (2013.01); *G01N 2291/044* (2013.01)

(58) Field of Classification Search
CPC ....... G01N 29/4436; G01N 2291/0226; G01H 15/00; G01H 3/04
See application file for complete search history.

(56) References Cited

OTHER PUBLICATIONS

PCT English Language Translation of the International Preliminary Report on Patentability, PCT/EP2017/072287, dated Mar. 28, 2019, 8 pages.

\* cited by examiner

METHOD AND DEVICE FOR DETERMINING AND/OR MONITORING THE BREAKDOWN VOLTAGE OF A TRANSFORMER OIL

CROSS-REFERENCE TO RELATED APPLICATIONS

This application represents the national stage entry of PCT International Application No. PCT/EP2017/072287 filed Sep. 6, 2017, which claims priority of German Patent Application 10 2016 117 188.3, filed Sep. 13, 2016, the contents of which are hereby incorporated by reference as if set forth in their entirety herein for all purposes.

The disclosure relates to a method and to a device for determining and/or monitoring the breakdown voltage of a transformer oil according to the preambles of the independent claims.

Devices of high-voltage technology, such as transformers, capacitors, Petersen coils and/or switches, are known from the state of the art and serve in particular, but by no means exclusively, to ensure a continuous electrical energy supply. Among these devices, transformers belong to the most important and also most expensive pieces of equipment in the electrical energy supply. To ensure a continuous and fault-free supply of electrical energy and to avoid economic losses, it is important that malfunctions which potentially occur in the operation of a transformer and which can cause outages are detected in time so as to be able to initiate suitable measures for rectification.

Typically, a combination of a liquid insulating material and a solid insulating material is used as insulant in transformers. For example, but by no means exclusively, the solid insulant is cellulose paper and/or chipboard. The liquid insulant, the transformer oil, is stable even at high temperatures and is used for insulation, spark suppression, lubrication and/or cooling of the transformer. In liquid-filled transformers of this kind in particular, defects in the solid and/or liquid insulant are almost exclusively due to the formation of gasses dissolved in the transformer oil and to a resulting increase in water content. One reason for the formation of the gasses is the decomposition of solid and/or liquid insulating materials, for example, which can be caused by partial discharge and circulating currents, local overheating due to short circuits, high transition resistance, strong eddy currents, and by arc discharges and/or arcing. The electrical and/or thermal energy input leads to a destruction of the long-chain oil molecules, which produces hydrogen and light hydrocarbon compounds, in particular. Additionally, the decomposition of cellulose produces carbon monoxide and carbon dioxide, which can occur in dissolved and/or undissolved form depending on the amount of the produced gasses. Thus, water molecules may be produced, as well, which lead to the undesired moisture content in the oil.

The water contained in the transformer oil is also problematic because the water enters the solid insulant, such as cellulose paper and/or chipboard, and washes the acids contained therein from production out into the transformer oil. This puts additional strain on the transformer, said strain being alternately strong or weak for various reasons, such as daytime-related temperature fluctuations (e.g., between day and night).

Hence, in order to maintain functionality and/or to ensure a continuous electrical energy supply, it is important to determine and/or monitor the breakdown voltage of the transformer oil. Thus, it is no surprise that a multitude of different methods and devices for determining the breakdown voltage of transformer oils are known from the state of the art, which determine the gasses dissolved in the transformer oil and/or the water content, for example, because both are known to have substantial impact on the breakdown voltage and thus indirectly on the life span and/or utilization time of the transformer. The reason for this is that water in the transformer leads to hydrolysis of the solid insulant and thus to a reduction of its degree of polymerization. However, all of these methods and devices have the disadvantage that sampling is required and that the breakdown voltage of the transformer oil is determined and/or monitored neither permanently nor on-line. It is not possible either to detect load peaks of the transformer in this way. Another problem with this is that transformer oil is highly hygroscopic, which means that sampling itself will distort the measured values.

Hence, there is great demand for a method and for a device for determining and/or monitoring the breakdown voltage of a transformer oil and thus indirectly for determining and/or monitoring the breakdown voltage of a device of high-voltage technology by means of which quick, reliable and sufficiently precise determination and/or monitoring of the breakdown voltage is ensured so as to avoid an unnecessary and expensive oil change and simultaneously ensure the continuous electrical energy supply. Moreover, the method and the device should be cost-effective in terms of implementation, work reliably, and be suitable for permanent determination and/or monitoring. Hence, the object of the disclosure is to provide a method and a device for determining and/or monitoring the breakdown voltage of a transformer oil in order to overcome the above-mentioned challenges and, above all, avoid a premature and/or unnecessary oil change and to ideally plan oil regeneration and/or maintenance and/or repair-related work so as to reduce downtimes of the device and the resulting costs to a minimum.

This object is attained in a surprisingly simple but effective manner by a method for determining and/or monitoring the breakdown voltage of a transformer oil and by a corresponding device according to the teaching of the independent main claims.

The disclosure proposes a method for determining and/or monitoring the breakdown voltage of a transformer oil that comprises the following steps:
a) performing an acoustic impedance measurement of the transformer oil, the impedance of a medium partially or entirely disposed in the transformer oil and capable of naturally vibrating and/or transmitting vibrations to the transformer oil being determined in at least one frequency band of defined frequency width; and
b) calculating a resonator quality factor for the frequency band based on the determination performed in step a); and
c) calculating an acoustic disbalance of the transformer oil based on the calculation performed in step b); and
d) ascertaining the breakdown voltage of the transformer oil based on the calculation performed in step c).

The method according to the disclosure is based on the idea that the combination of multiple physical relationships can be applied for a sufficiently precise determination and/or monitoring of the breakdown voltage of a transformer oil that can be performed on-line. For instance, it was found on the one hand that the breakdown voltage of a transformer oil is a function of the water content and of the total acid number of the transformer oil. Furthermore, it was found that the acoustic disbalance of a transformer oil is a function of the viscosity of the transformer oil, viscosity and interfacial tension in an oil being interdependent parameters.

Moreover, it was found that interfacial tension is a function of the water content and of the total acid number of the transformer oil. According to the disclosure, it was found that the breakdown voltage of a transformer oil is a function of the acoustic disbalance of the transformer oil, one or other dependencies off different physical parameters being negligible and/or leading to a tolerable error when implementing the method according to the disclosure.

Thus, it was found in connection with the present disclosure that the combination of performing an acoustic impedance measurement of the transformer oil, calculating a resonator quality factor and calculating an acoustic disbalance of the transformer oil suffices in order to determine the breakdown voltage of a transformer oil in an appropriately precise manner.

The term "method for determining and/or monitoring the breakdown voltage" refers to a method for ascertaining the breakdown voltage of the transformer oil once or repeatedly. Preferably, the method is based on ascertaining the change, preferably an improvement or a deterioration, of the breakdown voltage of the transformer oil. More preferably, said change is ascertained over time, preferably over the utilization time, the service life, and/or the downtime. Further preferably, the breakdown voltage of the transformer oil is determined at regular or irregular intervals or permanently so as to be able to quickly detect the change of the breakdown voltage. This is important in particular because transformer oil is not a static system. Additionally, the conditions and/or influences under which the change of the breakdown voltage of the transformer oil progresses or slows down can be tracked. Moreover, the development and/or cause of said change can be identified, allowing ideal planning and/or prediction of an upcoming maintenance interval and/or an upcoming transformer oil change or a corresponding transformer oil regeneration. In this regard, the method according to the disclosure may comprise additional steps that take place after or between the explicitly listed essential steps a) to d). Preferably, the method can be automated.

The term "determining the breakdown voltage" of the transformer oil refers to ascertaining the current breakdown voltage of the transformer oil. Determination is preferably performed semi-quantitatively, quantitatively, directly and/or indirectly. For instance, it is possible to ascertain the state of the transformer indirectly by ascertaining the breakdown voltage of the transformer oil.

The term "monitoring the breakdown voltage" refers to the tracking and/or prediction of the ascertained breakdown voltage of the transformer oil. For example, but by no means exclusively, monitoring can be displayed numerically and/or graphically. To increase the preciseness of monitoring, it preferably takes place at regular or irregular intervals or permanently. The advantage of longer monitoring is that a prediction of the breakdown voltage of the transformer oil is drastically improved.

A person skilled in the art understands that determination and/or monitoring will typically not be 100 percent correct. The term thus relates to a statistically significant probability regarding the preciseness of the ascertainment of the breakdown voltage and of the tracking and/or prediction of the ascertained breakdown voltage. A skilled person can determine whether such a determination and/or monitoring is statistically significant by methods known in the professional world without taking an inventive step. For example, statistical evaluation tools are to be mentioned, such as determination of the confidence interval, the p-value, the Student's t-test, the Mann-Whitney test, etc. The corresponding intervals are at least 90%, at least 95%, at least 97%, at least 98%, or at least 99% correct. The p-values are preferably 0.1, 0.05, 0.01, 0.005, or 0.0001. In connection with the disclosure, determination and/or monitoring of the breakdown voltage is at least 80%, at least 90%, at least 95%, at least 96%, at least 97%, at least 98%, at least 99%, at least 99.5%, or 100% correct.

The term "breakdown voltage", shortened to BDV, refers to the electrical field strength in the transformer oil that may exist at maximum without leading to electrical breakdown, electric arcs and/or arcing and the related outages and disadvantages. The breakdown voltage depends on different factors. The breakdown voltage can preferably be displayed graphically and/or in the form of an absolute value conforming to the current DIN standard, such as to DIN EN 60243-1:2012-05, for example.

The method according to the disclosure comprises a step a) of performing an acoustic impedance measurement of the transformer oil, the impedance of a medium partially or entirely disposed in the transformer oil and capable of naturally vibrating and/or transmitting vibrations to the transformer oil being determined in at least one frequency band of defined frequency width.

The term "acoustic impedance measurement" refers to the acoustic test of a fluid by drawing conclusions from the changes in resonance behavior of a medium partially or entirely disposed in the transformer oil and capable of naturally vibrating and/or transmitting vibrations to the transformer oil, such as a resonator, a resonance body, a resonance chamber, or a converter, in the ultrasonic frequency range (20 kHz to 1 GHz). The changes are based on the interactions between the molecules contained in the fluid and the elastic waves and/or the vibrations of said medium. The skilled person understands that the interaction of all components is calibrated. In this way, it is possible to use the acoustic impedance measurement to test the composition of the fluid and to draw conclusions as to the composition of the fluid. The fluid to be tested in connection with the disclosure is preferably a transformer oil.

In connection with the present disclosure, it was found that when the elastic wave propagates through the transformer oil and/or a corresponding medium is disposed in the transformer oil, in which a molecular balance prevails, the balance depends on the effect of the frequency of the wave and/or vibration. The substantial aspect is that the period of the elastic wave and/or of the vibration is much longer than the relaxation time for the change in equilibrium position, which is subsequently disturbed by the wave and/or by the vibration. On the other hand, if the period of the wave and/or of the vibration is much shorter than the relaxation time, the wave and/or the vibration will not disturb the balance. Consequently, the balance remains undisturbed. If the period is similar to the relaxation time, changes in propagation speed and in the coefficient of absorption of the elastic wave and/or of the vibration will occur. For example, but by no means exclusively, relaxation time and the speed constants of the balance can be determined from the measurements of the changes, as can cycle time, frequency shift and/or damping.

Preferably, the acoustic impedance measurement relates to ultrasonic frequencies, more preferably to frequencies of 75 kHz to 750 kHz. Further preferably, the acoustic impedance measurement is performed in at least one frequency band. More preferably, the acoustic impedance measurement is performed in two, three, four, five, six, seven, eight, nine, ten, or more frequency bands, wherein it was found to be a substantial aspect in connection with the disclosure that each frequency band has a defined frequency width, more preferably in a defined frequency range. Hence, it is understandable that each frequency band has the same frequency width.

In another step, a resonator quality factor for the frequency band is calculated based on the previously performed determination. The term "resonator quality factor", shortened to Q-factor, is a dimensionless parameter that describes the degree of underdamping of a medium capable of naturally vibrating and/or transmitting vibrations to the transformer oil and thus characterizes the bandwidth thereof relative to its center frequency.

Additionally, it was found in connection with the disclosure that for small damping values a (high impedance values), it is possible to determine the relationship between the half-power bandwidth HPB or "3 dB bandwidth" Δf of a specific amplitude and the frequency $f_n$ of maximum width as known from the state of the art. In this regard, the following Formula (1) applies:

$$\frac{\alpha \lambda}{\pi} = \frac{\Delta f}{fn} = \frac{1}{Q}$$

wherein
α is the damping value, and
Δf is the width of the amplitude, and
$f_n$ is the frequency of maximum width, and
Q is the resonator quality factor.

Preferably, it follows from Formula (1) that the resonator quality factor Q of an ideal resonator can be achieved by liquid damping. The resonator quality factor Q of the real resonance system $Q_{real}$ is inversely proportional to the total energy loss in the resonance system, meaning the share of all types of energy losses, such as liquid damping and additional losses from beam divergence, scattering, friction effects, imperfect reflection at the surface, and/or coupling losses.

Further preferably, the resonator quality factor is calculated according to Formula (2):

$$Q_n = \frac{f_0}{\Delta f}$$

wherein
Qn is the resonator quality factor for the frequency band, and
$f_0$ is the frequency of maximum amplitude, and
Δf is the defined resonance width in Hz.

Furthermore, an acoustic disbalance, shortened to AcDis, of the transformer oil is calculated based on the previously performed calculation of the resonator quality factor. Preferably, the acoustic disbalance is calculated according to Formula (3):

$$AcDis = a + b * Q_n$$

wherein
AcDis is the acoustic disbalance, and
a is an empirically ascertainable constant or calibration value, and
b is an empirically ascertainable constant or calibration value, and
Qn is the resonator quality factor for the frequency band.

A skilled person understands that the calibration values a and b depend on the medium capable of naturally vibrating and/or transmitting vibrations to the transformer oil, such as a resonator and/or the piezoelectric material used, meaning they are not ascertained before the calibration process. The manner in which calibration is performed is generally optional and is subject to the skilled person's expertise.

According to the disclosure, it was found that the breakdown voltage of a transformer oil is a function of the acoustic disbalance of the transformer oil, one or other dependencies of different physical parameters being negligible and/or leading to a tolerable error when implementing the method according to the disclosure. Hence, the breakdown voltage of the transformer oil can be ascertained based on the previously performed calculation of the acoustic disbalance.

In connection with the disclosure, determination, calculation and/or ascertainment are preferably performed with computer assistance. For a computer-assisted performance of these steps, such as steps a), b), c), and/or d), all means known to the skilled person are conceivable, such as computers and/or a computer program. A computer program can additionally evaluate the corresponding result, automatically providing an assessment of the value, for example. Furthermore, it is conceivable, for example, that the steps a), b), c), and/or d) are supported by an assessing unit, an analyzing unit, and/or an evaluating unit. Preferably, it is also possible to take successive values into account in a comparison, allowing a prediction as to how the breakdown voltage will change as a function of time based on said comparison. Thus, it is conceivable that a small and insignificant change, a great and significant change and/or no change in the successive values is indicative of a specific breakdown voltage of the transformer. A change in the successive values can preferably be an improvement and/or a deterioration of said values. In this context, it is conceivable that the result of the comparison can be outputted as an indication of time, such as in years, months, days, hours and/or minutes, as an absolute value and/or a relative value.

The term "comparison" as used herein refers to the comparison of corresponding parameters and/or values. For instance, it is conceivable that absolute values are compared with each other. The same applies to relative values and/or to an intensity signal. It also conceivable for the comparison to be performed based on an empirically ascertained model for reference transformer oils.

The term "transformer oil" refers to a liquid insulating material which is stable at high temperatures and which is used for insulation, spark suppression, lubrication and/or cooling of a device of high-voltage technology, such as a transformer, a capacitor and/or a switch. For example, but by no means exclusively, the liquid insulating material is a highly refined mineral oil, a gas-to-liquid (GTL), a low-viscosity silicone oil, a natural oil, a vegetable oil, a synthetic organic ester, such as a saturated pentaerythritol tetra-fatty acid ester, and/or an amino-acid compound.

Thus, by means of the method according to the disclosure, it is possible to easily, quickly and reliably determine and/or monitor the breakdown voltage of the transformer oil in order to, for example, make an assessment regarding the breakdown voltage of the corresponding device of high-voltage technology. It is possible to perform this determination and/or monitoring in a running device, i.e., on-line. Advantageously, the method is designed in such a manner that sampling with its known disadvantages can be entirely omitted. In this way, it is possible to avoid premature and/or unnecessary and expensive oil change and to simultaneously ensure a continuous electrical energy supply at all times.

Additionally, it is possible to ideally plan the downtimes of the device required for maintenance, regeneration and/or repair so as to avoid unnecessary downtimes and/or costs.

Advantageous embodiments of the disclosure, which can be realized individually or in combination, are illustrated in the dependent claims.

It is conceivable that an embodiment of the disclosure comprises an additional step c1) after step c):

c1) registering at least one value of at least one characteristic physical property of the transformer oil.

In connection with the present disclosure, it was further found that while the individual information on the acoustic disbalance of the transformer oil suffices to ascertain the breakdown voltage to sufficient precision, it has also been found that at least one value of at least one characteristic physical property of the transformer oil is to be registered and used in said ascertainment in order to fix the "shifting point". It was found in particular that if the acoustic disbalance of the transformer oil "slides" along an axis of a 2-dimensional function, i.e., a curve composed of the total acid number and the water content, only the at least one value of the at least one characteristic physical property forces the behavior of the function toward an improved, sufficiently precise ascertainment of the breakdown voltage. Hence, it is understandable that the breakdown voltage of the transformer oil is ascertained based on the calculated acoustic disbalance and on the registered at least one value of the at least one characteristic property, wherein the rule applies that the preciseness of the ascertainment in step d) increases as the number of registered values grows.

The term "characteristic physical property" refers to a physical property that is typical of the transformer oil and from which the breakdown voltage of the transformer oil or the state of the transformer can be derived directly or indirectly. Preferably, said property changes as a function of the aging process of the transformer oil, the change preferably being an improvement or a deterioration. Characteristic physical properties of the transformer oil of this kind and their registration, determination and/or calculation are well known to the person skilled in the art, such as density, color, refractive index, temperature, solubility in water, water content, interfacial tension, viscosity, relative and/or absolute moisture or saturation, loss factor, acid number, electric constant, electrical conductivity, and/or concentration of at least one fluid. Additionally, other properties not listed here are conceivable, such as a resonator quality factor for a frequency band and/or an acoustic disbalance for a transformer oil.

It is conceivable that 2, 3, 4, 5, 6, 7, 8, 9, 10, 11, 12, 13, 14, 15, 16, 17, 18, 19, 20 or more values of the same characteristic physical property are registered. Preferably, it is conceivable that a mean value of said values is used. Alternatively, it is also conceivable that 2, 3, 4, 5, 6, 7, 8, 9, 10, 11, 12, 13, 14, 15, 16, 17, 18, 19, 20 or more values of different characteristic physical properties are registered. The number of different characteristic properties of the transformer oil having to be registered is subject to the skilled person's assessment. This is because a physical property depends on and/or can be influenced by different factors, whose additional registration adds to further improvement of the determination and/or monitoring.

In an alternative of the embodiment of the disclosure, it is conceivable that at least one value of the temperature of the transformer oil is registered in step c1).

Registration of the temperature can be realized in an advantageously easy, quick and reliable manner. Hence, it is understandable that the breakdown voltage of the transformer oil is ascertained based on the calculated acoustic disbalance and on the at least one registered value of the temperature.

In yet another alternative of the embodiment of the disclosure, it is conceivable that the method comprises an additional step c2) after step c1):

c2) calculating the water content and/or the relative saturation in the transformer oil.

In connection with the present disclosure, it was additionally found that for fixing the "shifting point", it is helpful to register additional values for characteristic properties of the transformer oil. This is because ascertaining the breakdown voltage of the transformer oil is difficult because of the changing transformer oil if the acoustic disbalance moves diagonally, i.e. along both axes of a 2-dimensional function, i.e. a curve composed of the total acid number and the water content. Hence, it was found that ascertaining the breakdown voltage can be drastically improved once more by directly calculating the water content and/or the relative saturation. Hence, preferably, the water content and/or the relative saturation in the transformer oil are calculated in an additional step c2).

Furthermore preferably, it is conceivable in this regard that the solubility of water in mineral oil is calculated first. Solubility is defined as the total amount of water that can be dissolved in the mineral oil at a specific temperature. Preferably, the solubility of water is calculated by means of Formula (4):

$$\log S_0 = \frac{1567}{K} + 7.0895$$

wherein
$S_0$ is the solubility of water in mineral oil, and
K is the temperature in Kelvin (° C.+273).

Further preferably, it is conceivable in this regard that the relative saturation of the transformer oil is calculated next. According to the disclosure, it was found that calculating the relative saturation is sufficient for quick ascertainment of the breakdown voltage. Relative saturation is defined as the actual amount of water measured in the transformer oil relative to the degree of solubility at that temperature. The relative saturation, which is expressed in percentages, is the water content in the oil relative to the solubility or the water content that the oil can absorb at the measured temperature, as preferably calculated according to Formula (5):

$$RS = \frac{W_C}{S_0}$$

wherein
RS is the relative saturation, and
$W_C$ is the water content in ppm, and
$S_0$ is the solubility of water in mineral oil in ppm.

In connection with the disclosure, it was found that with the aid of Formula (5), it is possible to directly arrive at the calculation of the water content ratio based on the relative saturation and/or the specific temperature, which leads to improved ascertainment of the breakdown voltage. Preferably, the water content is calculated by means of Formula (6):

$$W_C = RS * 10^{\left(\frac{-1567}{K+7.0895}\right)}$$

wherein $W_C$ is the water content in ppm, and

RS is the relative saturation, and $S_0$ is the solubility of water in mineral oil in ppm; and K is the temperature in Kelvin (° C.+273).

Hence, it is understandable that the breakdown voltage of the transformer oil is ascertained based on the calculated acoustic disbalance, the registered at least one value of the at least one characteristic property, such as the temperature, and the calculated water content or based on the calculated acoustic disbalance and the calculated water content while neglecting the temperature.

In another configuration, it is conceivable that, in step a), the impedance is determined in four frequency bands each having a defined frequency width of 75 kHz. This configuration allows, for example, but by no means exclusively, performing the acoustic spectroscopy in four frequency bands each having the defined frequency width of 75 kHz, such as in the defined frequency range of 75 kHz to 750 kHz, such as in the manner of frequency band 1 (125 kHz to 200 kHz), frequency band 2 (225 kHz to 300 kHz), frequency band 3 (325 kHz to 400 kHz) and frequency band 4 (525 kHz to 600 kHz). Preferably, a new measurement is performed at the frequency that corresponds to the defined frequency width of 75 kHz per frequency band.

In another embodiment of the disclosure, it is conceivable that the method additionally comprises the step of e) displaying the ascertainment performed in step d).

This configuration allows the breakdown voltage of the transformer oil to be numerically and/or graphically displayed so as to achieve easier understanding of the ascertainment in step d) in this way. The skilled person knows suitable means for displaying an output of a value. Step e) can be supported by an output unit.

It is assumed that the definitions and/or explanations of the terms mentioned above apply to all aspects described hereinafter in this description, unless indicated otherwise.

Furthermore, according to the disclosure, a device for determining and/or monitoring the breakdown voltage of a transformer oil according to any one of the method claims is proposed, said device comprising:

a) a first medium for performing an acoustic impedance measurement of the transformer oil, wherein the impedance of the first medium, which is partially or entirely disposed in the transformer oil and capable of naturally vibrating or transmitting vibrations to the transformer oil, is determined in at least one frequency band of defined frequency width; and b) at least one analyzing and/or evaluating unit for calculating a resonator quality factor for the frequency band, for calculating an acoustic disbalance of the transformer oil and for ascertaining the breakdown voltage of the transformer oil.

The device according to the disclosure is preferably self-learning and/or self-calibrating so that best possible determination and/or monitoring of the breakdown voltage of the transformer oil can be achieved.

The term "first medium" refers to any medium known to the skilled person from the state of the art that is partially or entirely disposed in the transformer oil and capable of naturally vibrating and/or transmitting vibrations to the transformer oil. It is understood that at least one of the natural frequencies of the first medium is in the ultrasonic frequency range, preferably in the range of the frequency band. Preferably, the first medium is a resonator, a resonance body, a resonance chamber or a converter, such as a sound converter. More preferably, the resonator is an oscillating, piezoelectric and/or aluminum-coated resonator. An aluminum-coated piezoelectric resonator has the advantage that it can be used for an ultrasonic relaxation method with respect to the energy transfer between translational and vibrational degrees of freedom for measuring a type of acoustic disbalance and directly for calculating the water/total acid balance. Further preferably, the sound converter is a mechanical, electrical, magnetic, and/or piezoelectric sound converter.

The term "analyzing and/or evaluating unit" refers to a unit that is capable of evaluating, calculating, comparing and/or ascertaining a resonator quality factor for a frequency band, an acoustic disbalance of the transformer oil, at least one value of at least one characteristic property and/or the breakdown voltage of the transformer. Suitable analyzing and/or evaluating units, such as a computer and/or a computer program, are known to the person skilled in the art. A computer program can additionally assess the result of the comparison. It is understood that the device can comprise more than one analyzing and/or evaluating unit.

The device according to the disclosure has the advantage that it exhibits sufficiently precise sensitivity for determining and/or monitoring the breakdown voltage of the transformer oil during operation, i.e., on-line, while simultaneously being robust enough to withstand the everyday conditions of a working transformer in the long term.

Advantageous embodiments of the disclosure, which can be realized individually or in combination, are illustrated in the dependent claims.

In an embodiment of the disclosure, it is conceivable that the device comprises a second medium for registering at least one value of at least one characteristic physical property of the transformer oil.

The term "second medium" refers to any medium known to the skilled person from the state of the art that is capable of registering at least one value of at least one characteristic physical property of the transformer oil at at least one point in time, such as density, color, refractory index, temperature, solubility in water, water content, interfacial tension, viscosity, relative and/or absolute moisture or saturation, loss factor, acid number, electric constant, electric conductivity and/or concentration of at least one fluid. Moreover, other properties not listed here are conceivable. Preferably, the point in time is registered simultaneously. Preferably, the second medium is a sensor, such as a pressure, moisture and/or temperature sensor.

In yet another embodiment of the disclosure, it is conceivable that the device comprises an output unit for displaying the ascertainment performed by means of the analyzing and/or evaluating unit.

The term "output unit" refers to a unit which is capable of displaying the evaluated, calculated, compared and/or ascertained values, results and and/or breakdown voltage of the transformer oil. This configuration allows the values, the results and/or the breakdown voltage of the transformer oil to be numerically and/or graphically displayed so as to achieve easier understanding of the ascertainment in step b) in this way. The person skilled in the art knows a suitable output unit for displaying.

In another embodiment of the present disclosure, it is conceivable that the first medium, the second medium, the analyzing and/or evaluating unit and/or the output unit are disposed in one component. This configuration offers the advantage that the device is compact and very easy do handle and easy to transport.

In an alternative configuration of this embodiment, it is conceivable that the component is a measuring chamber, a stick, and/or an adapter. This configuration offers the advantage that the device can be easily, quickly and reliably connected to a device of high-voltage technology, such as a transformer. Further preferably, the device is connected directly, such as by cable or via an adapter.

In another configuration, it is conceivable that the device comprises a heating device. This configuration has the advantage that the device can be heated prior to performing the first measurement, thus ensuring that the media located in the device are always dry. This helps improve the measured values significantly because distortions are typically due to the media being penetrated by moisture. Heating devices of this kind, such as a heating coil and/or a Peltier element, are well known to the person skilled in the art.

Furthermore, according to the disclosure, a device of high-voltage technology, in particular a transformer, a capacitor, a Petersen coil and/or a switch, comprising transformer oil and a means for connecting the same to the device according to any one of the preceding claims is proposed, the connection being a direct connection.

The term "direct connection" refers to any immediate connection of the means to the device. A connection of this kind can be realized, for example, but by no means exclusively, by way of a recess and/or a protrusion on the means and a correspondingly configured device. Furthermore, it is conceivable that a direct connection is a USB, TCP/IP, or MODBUS connection or any other wired or wireless connection. This configuration allows simple, quick and reliable connection of the device for determining the breakdown voltage of the transformer oil to a device of high-voltage technology in order to determine and/or monitor the state thereof in a quick, reliable and appropriately precise fashion.

Other details, features and advantages of the disclosure are apparent from the following description of the preferred embodiments in conjunction with the dependent claims. The respective features can be realized on their own or multiple features can be realized in combination with one another. The disclosure is not limited to the embodiments. The embodiments are schematically illustrated in the figures. Identical reference signs in the individual figures refer to identical elements or to elements of identical or mutually corresponding function.

Figure 2:
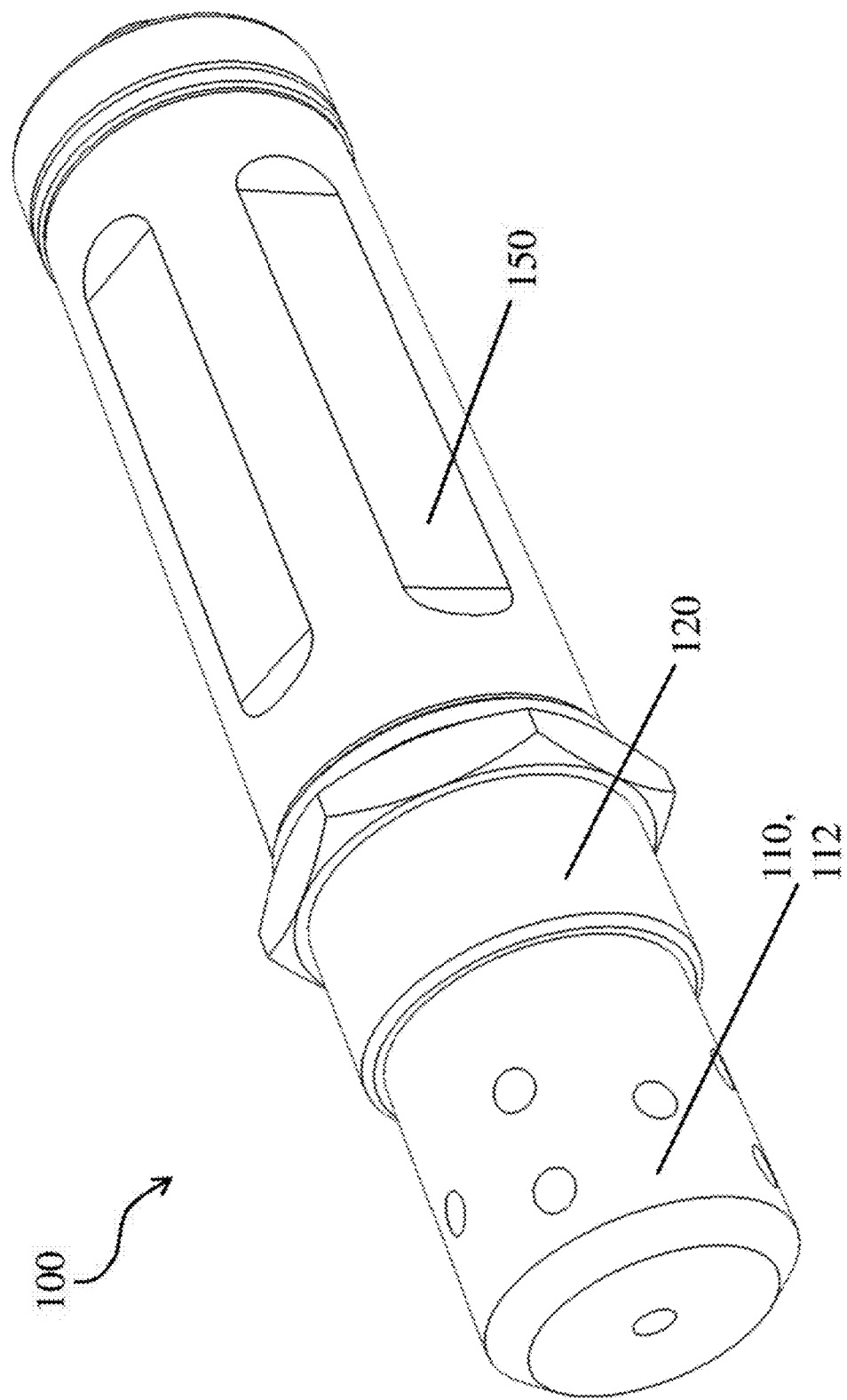
Figure 3:
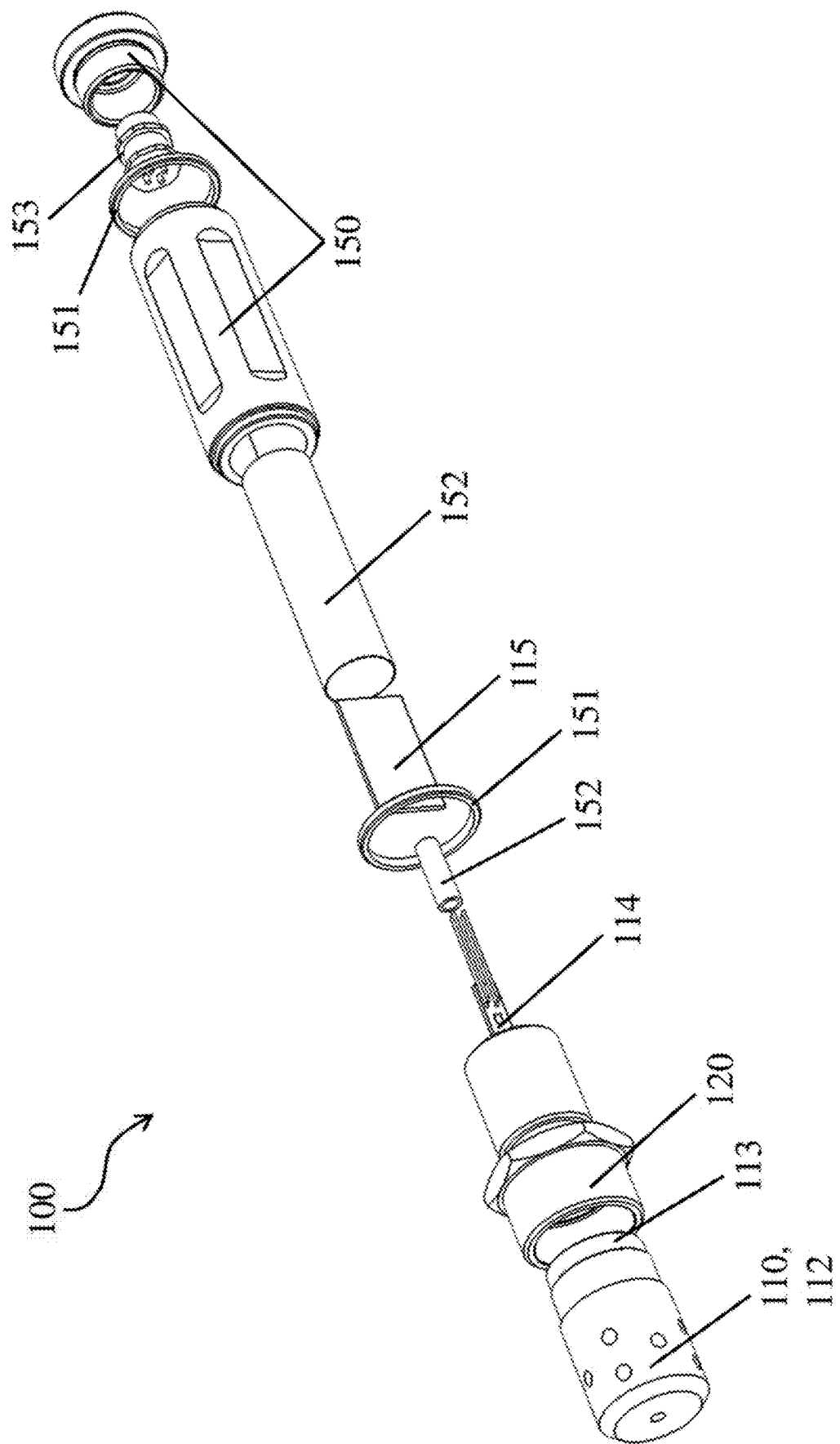
Figure 4:
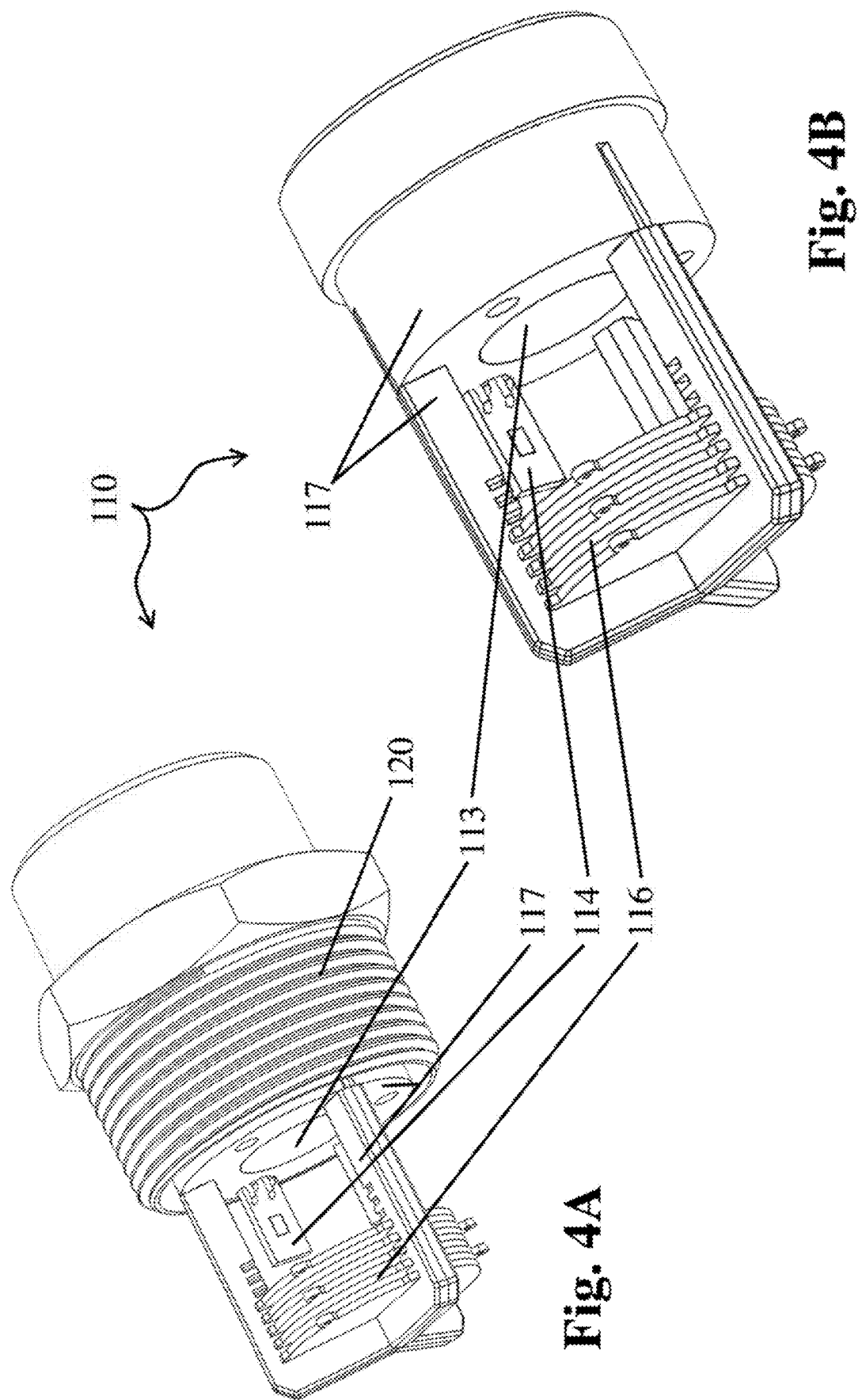
Figure 5:
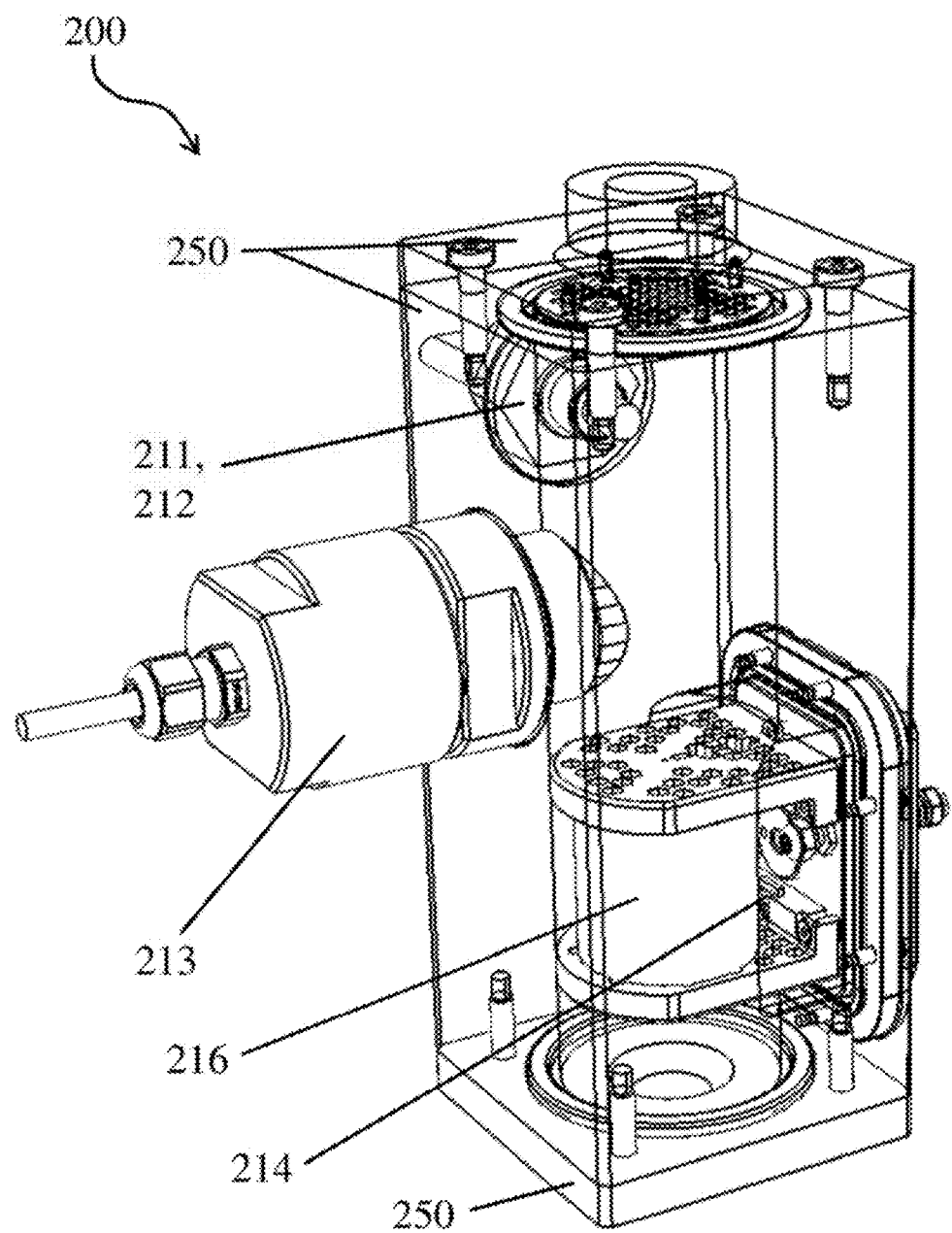
Figure 6:
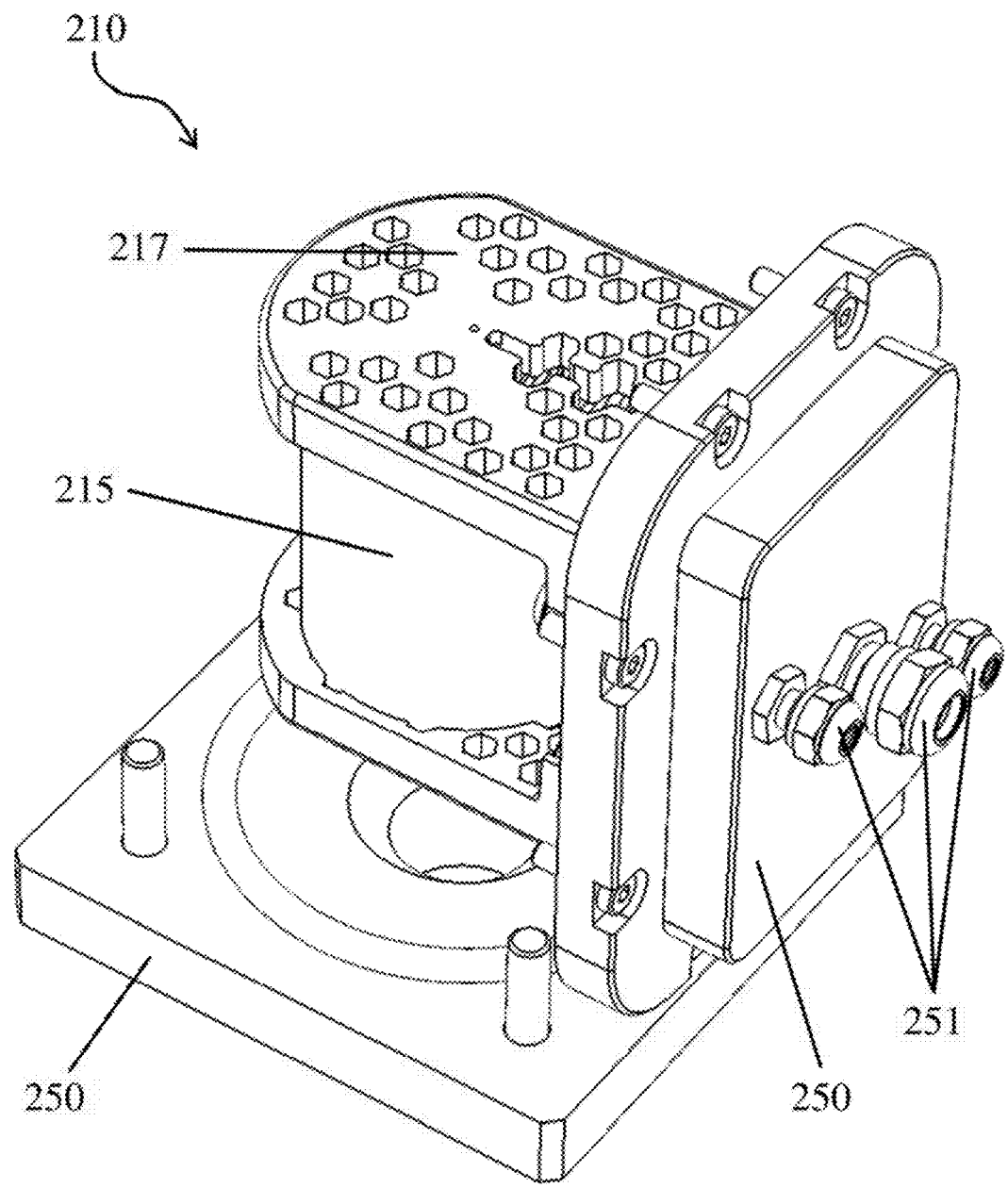
Figure 7:
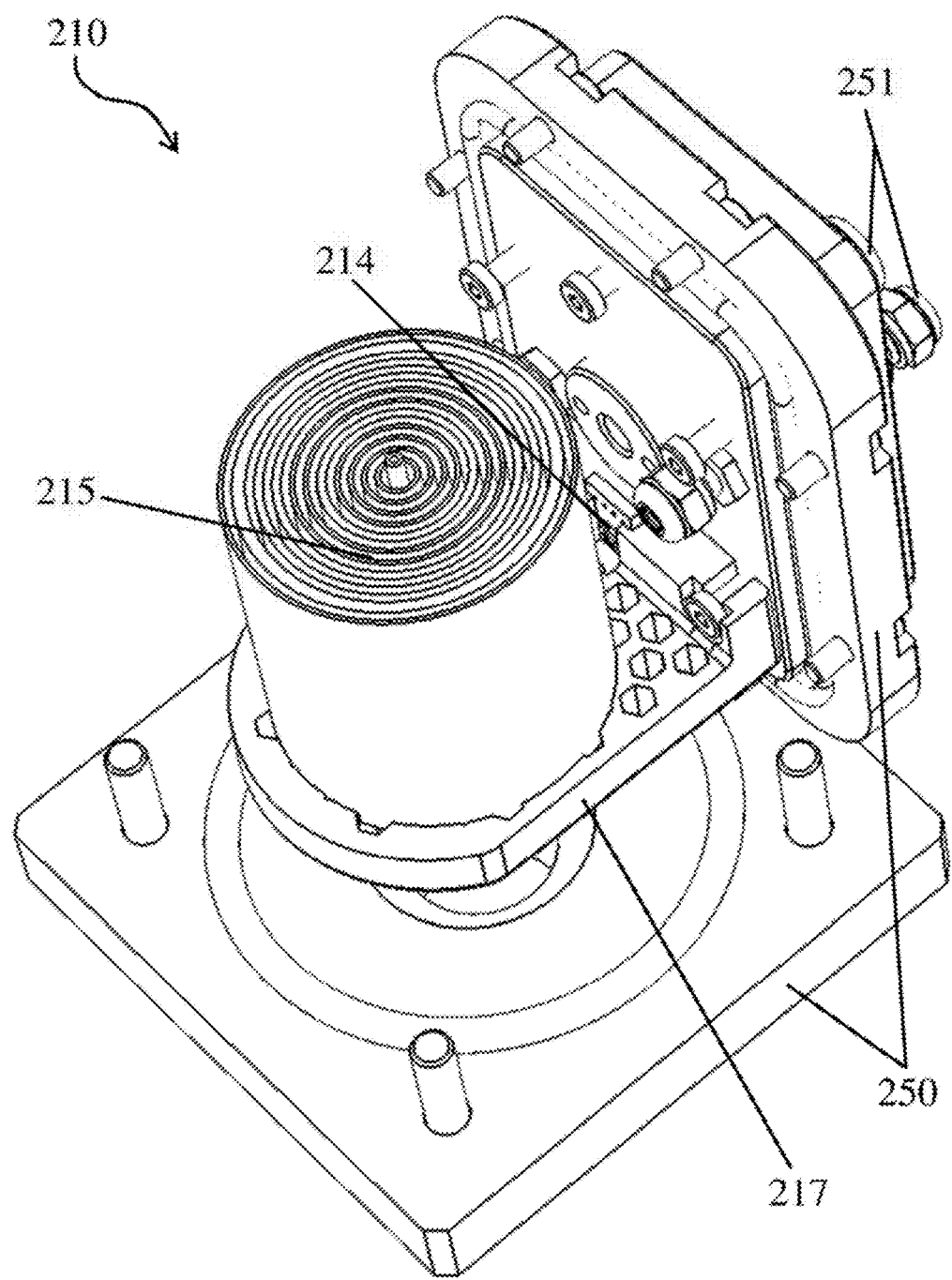
Figure 8:
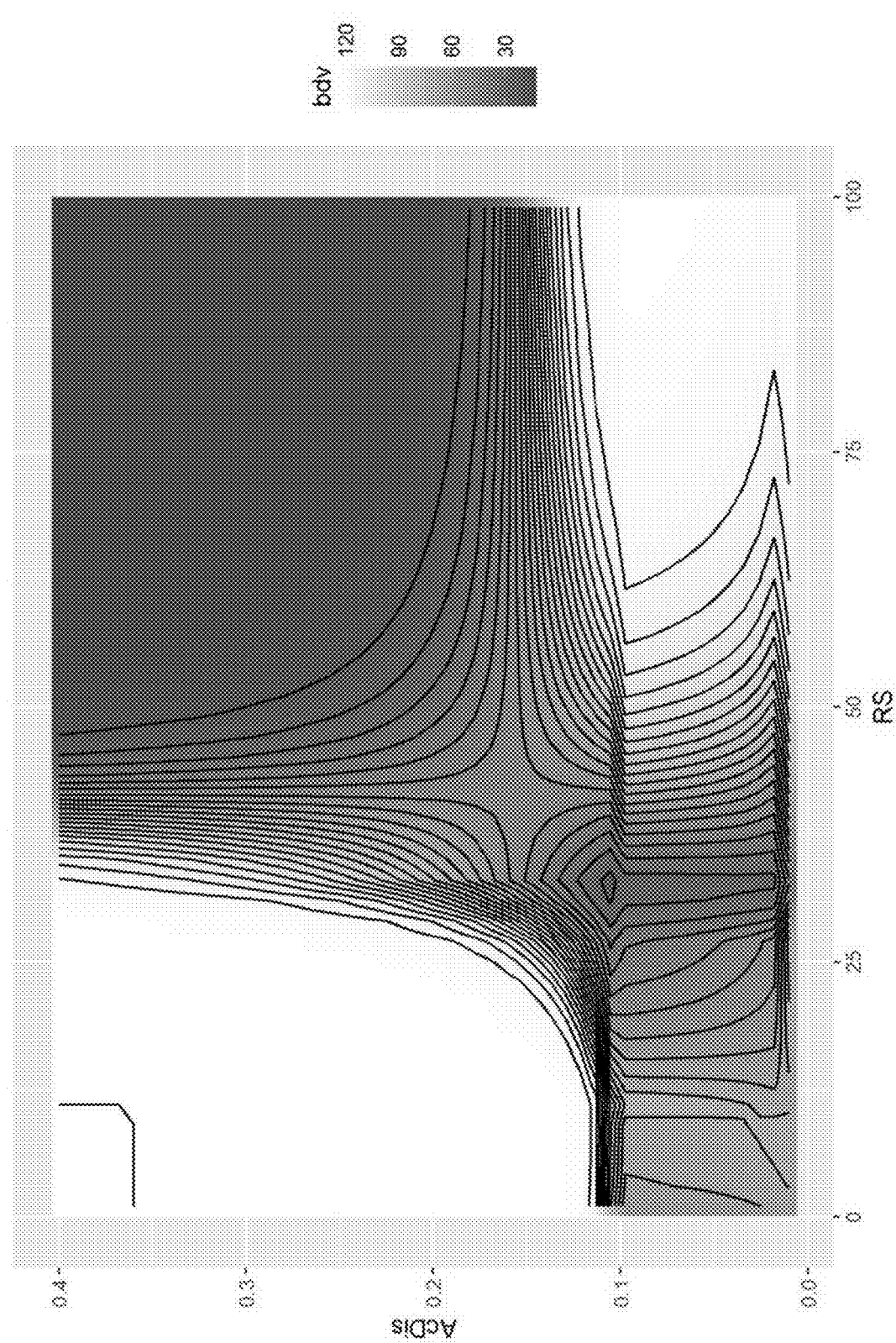
Figure 9:
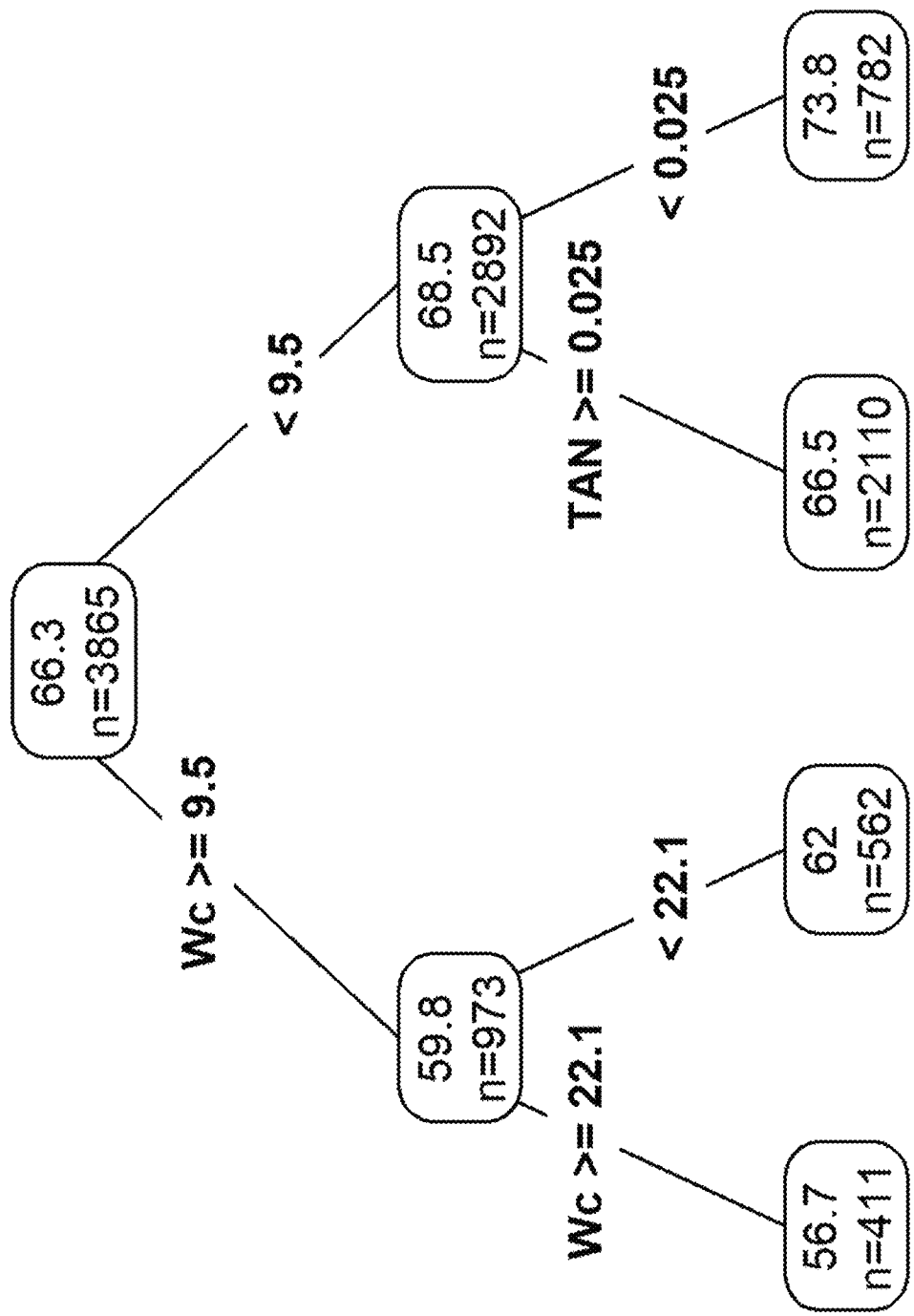
Figure 10:
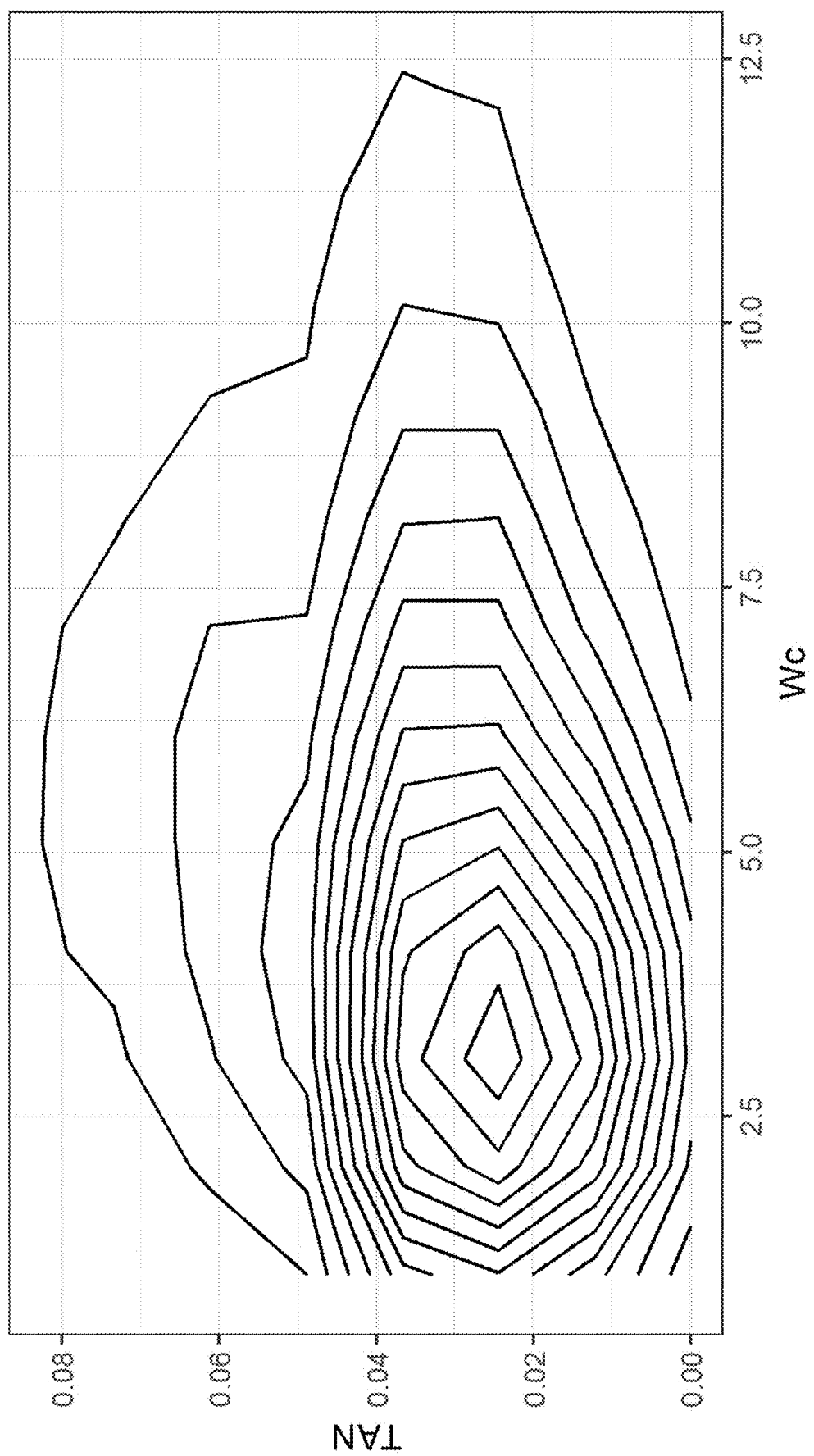
Figure 11:
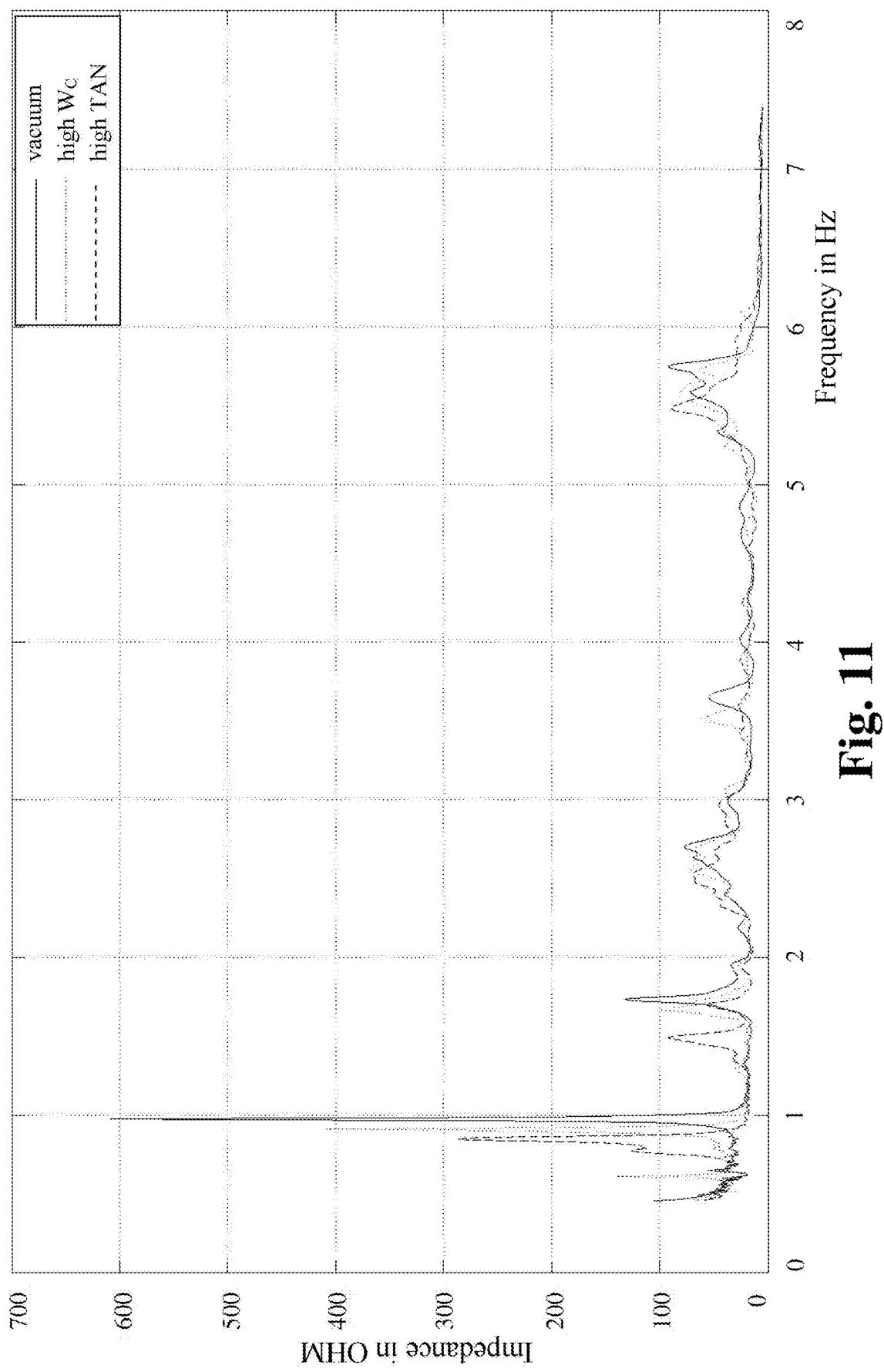
Figure 12:
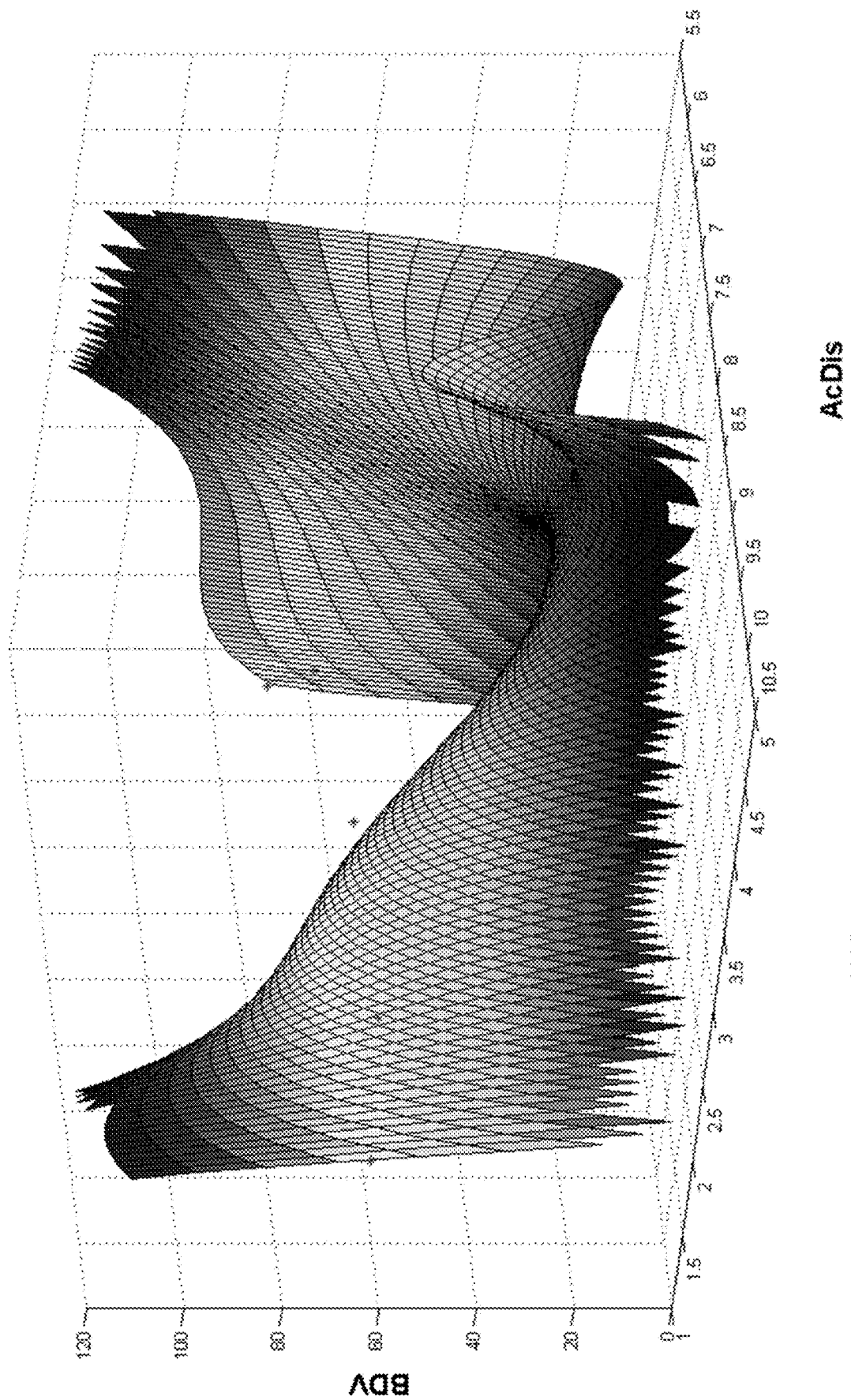

FIG. 1 shows an isometric illustration of a first embodiment of a device according to the disclosure with a protective cover; and FIG. 2 shows another isometric illustration of the first embodiment in a device according to the disclosure without a protective cover; and FIG. 3 shows an exploded illustration of the first embodiment of a device according to the disclosure without a protective cover; and FIG. 4 shows an isometric illustration of the sensor portion of the first embodiment of a device according to the disclosure with different attachment portions (FIGS. 4a and 4b); and FIG. 5 shows an isometric illustration of a second embodiment of a device according to the disclosure; and FIG. 6 shows an isometric illustration of a sensor portion of the second embodiment of a device according to the disclosure; and FIG. 7 shows another isometric illustration of a sensor portion of the second embodiment of a device according to the disclosure; and FIG. 8 shows a matrix graphic of an exemplary calculation of the determination of the breakdown voltage of a transformer oil; and FIG. 9 shows a regression tree for the calculation of the breakdown voltage of multiple tested transformer oils; and FIG. 10 shows a 2-dimensional function of the total acid number (TAN) and the water content ($W_C$) of multiple tested transformer oil samples; and FIG. 11 shows a spectral density function of an aluminum-coated piezoelectric resonator in contact with a transformer oil; and FIG. 12 shows a polynomial approximation for the breakdown voltage (values for calculation exponentially scaled) based on specific water content values and acoustic disbalance values.

FIG. 1 shows an isometric illustration of a first embodiment of a device 100 according to the disclosure for determining and/or monitoring the breakdown voltage of a transformer oil, the device 100 being realized in the form of a stick 100. As clearly visible in FIG. 1, stick 100 has a sensor portion 110 provided with a protective cover 111. Additionally, an attachment portion 120 for secure attachment of stick 100 to a transformer is provided on stick 100, said attachment portion 120 being realized in the form of a 1.5-inch pipe thread. Housing 150 of stick 100 protects the electronics, in particular against undesired electrical and/or to electromagnetic effect, as well as serving as insulation and as a communication device and may be made from any suitable material. Preferably, housing 105 is made of a metallic material guaranteeing electromagnetic compatibility.

In FIG. 2, an alternative configuration of the first embodiment of a device 100 according to the disclosure for determining and/or monitoring the breakdown voltage of a transformer oil is shown, which is also realized in the form of a stick 100. As clearly visible in FIG. 2, stick 100 has a sensor portion 110 comprising a resonance chamber 112. Resonance chamber 112 is visible because no protective cover is shown in the alternative configuration of the first embodiment. Additionally, stick 100 has an attachment portion 120 for secure attachment of stick 100 to a transformer, said attachment portion 120 being realized, for example, as a 1.0-inch pipe thread in this alternative. Likewise, a housing 150 is comprised.

FIG. 3 shows an exploded illustration of the alternative configuration of the first embodiment of device 100 according to the disclosure as shown in FIG. 2, FIG. 3 showing the internal structure of device 100. As clearly visible, critical and sensitive components of device 100 are covered and protected by a robust and sophisticated interaction between disposition and housing elements 150, 151 and 152. This stick 100 also has a sensor portion 110 and a resonance chamber 112, which is visible because the protective cover is not illustrated. Furthermore, an acoustic converter 113 and an attachment portion 120 are comprised, the latter, as also shown in FIG. 2, being realized in the form of a 1.0-inch pipe thread, for example.

Furthermore, it is clearly visible in FIG. 3 that a moisture and/or temperature sensor 114 and the resonator are accommodated in resonance chamber 112 and acoustic converter 113. Additionally, the corresponding electronics 115 are comprised. Electronics 115 are surrounded by an insulation 152, which is made of plastic, for example. Housing 150 additionally comprises multiple insulating elements 152, which can be made from plastic, for example. Furthermore, multiple spacer rings 151 and a cable connector 153 are comprised, so as to enable connection to sensor electronics 115 of stick 100, such as via Modbus.

In FIG. 4, two alternative configurations of a first embodiment of sensor portion 110 of device 100 according to the disclosure are shown. As clearly visible in FIG. 4a and FIG. 4b, sensor portion 110 comprises multiple capacitor plates 116, which are part of a dielectric sensor. Furthermore, a moisture and/or temperature sensor 114 and an acoustic converter having a resonance chamber 113 are comprised. Retaining element 117 can be insulating and can be made of plastic, for example. FIG. 4a additionally illustrates an attachment portion 120, which is realized in the form of a 1.5-inch pipe thread, for example, like in FIG. 1.

FIG. 5 shows a second embodiment of a device 200 according to the disclosure for determining and/or monitoring the breakdown voltage of a transformer oil, said device 200 being realized in the form of a measuring chamber 200. As is clearly visible in FIG. 5, measuring chamber 200 has multiple sensor portions; for instance, a density and/or viscosity sensor 211 and/or an optical sensor 212 are disposed in one sensor portion. In another sensor portion, an acoustic sensor 213 and, furthermore, a dielectric sensor 216 and a moisture and/or temperature sensor 214 are disposed. Moreover, measuring chamber 200 has a housing 250.

In FIG. 6 and FIG. 7, one of the sensor portions 210 of the measuring chamber as shown in FIG. 5 is illustrated in detail. As clearly illustrated in FIGS. 6 and 7, a retaining element 217 is comprised, which is insulating and can be made of plastic, for example. Additionally, capacitor plates 215 (realized as a cylinder capacitor made of concentric tubes) is visible in the two figures, said capacitor plates 215 being part of the dielectric sensor. In FIG. 7, moisture and/or temperature sensor 214 is visible, as well. Furthermore, housing 250, which serves as insulation of the measuring chamber from FIG. 5, as well as cable bushings 251 for connection thereto are visible in FIG. 6 and FIG. 7.

FIG. 8 shows a graphic illustration in the form of a matrix graphic for a calculation example of the determination of the breakdown voltage (BDV) of a transformer oil based on a 2-dimensional function composed of the relative saturation (RS) and of the acoustic disbalance (AcDis). The isogens illustrated in the matrix each correspond to 5 [kV].

In the first stage of the 2-dimensional function, function bdvL (RS, AcDis) is calculated, which depends on main function h(x). In this regard, the following Formula (1) applies:

$$h(x) = \begin{cases} x & \text{if } x \geq 0 \\ 0 & \text{if } x < 0 \end{cases}$$

wherein
h is the main function, and
x is the argument value.

According to Formula (1), the main function has different arguments. If the argument value is x≥0, the function will apply that value. If the argument value is x<0, the value is zero and the term is deleted.

Based on this Formula (1), a calculation example of the determination of the breakdown voltage (BDV) is shown below in Formula (2).

Formula (2) is:

bdvL(RS,AcDis)=−0.10−0.23h(0.096885−log$_{10}$(RS))−96.79h(log$_{10}$(RS)−0.986885)−9.38h(log$_{10}$(RS)−1.03756)−19.27h(log$_{10}$(RS)−1.43403)+30.27h(log$_{10}$(RS)−1.51121)+0.21h(−0.987312−log$_{10}$(AcDis))+67.11h(log$_{10}$(AcDis)+0.987312)−169.59h(log$_{10}$(RS)−0.986885)*h(log$_{10}$(AcDis)+1.44532)+169.36h(log$_{10}$(RS)−0.986885*h(−1.44532−log$_{10}$(AcDis))−119.70h(log$_{10}$(RS)−0.986885)*h(log$_{10}$(AcDis)+0.996463)+179.58h(log$_{10}$(RS)−0.986885*h(log$_{10}$(AcDis)+1.99022)+0.02h(1.04391−log$_{10}$(RS))*h(−0.987312−log$_{10}$(AcDis))+13.10h(log$_{10}$(RS)−1.04391)*h(−0.987312−log$_{10}$(AcDis))+11.55h(log$_{10}$(RS)−1.43403)*h(log$_{10}$(AcDis)+2.00147 wherein
bdvL is a non-standardized intermediate value of the breakdown voltage,
h is the main function with the argument values x,
wherein
x=RS is the relative saturation, and
x=AcDis is the acoustic disbalance.

In the second stage of the 2-dimensional function, the value bdvL calculated by means of Formula (2) is standardized according to current standard DIN EN 60243-1:2012-05 (cf. "Electrical strength of insulating materials—Test methods—Part 1: Tests at power frequencies" (IEC 112/199/CDV:2011)). Standardizing takes place according to Formula (3):

$$BDV = 10 + \frac{110}{1 + \exp(-bdvL)} [kV]$$

wherein
bdvL is a non-standardized intermediate value of the breakdown voltage, and
BDV is the breakdown voltage.

More information can be found in the known standard work Friedman (1991) Multivariate Adaptive Regression Splines (with discussion) Annals of Statistics 19/1, 1-141, (https://statistics.stanford.edu/research/multivariate-adaptive-regression-splines).

FIG. 9 shows an overview of the method and of the device. By means of said overview, it can be shown that in order to achieve a drastically improved ascertainment of the breakdown voltage (BDV), no more than two of the described parameters need to be measured because there is close correlation between the water content ($W_C$), the total acid number (TAN) and the breakdown voltage in the tested transformer oil samples. By evaluating more than 3800 lab samples from more than 900 transformers, the regression tree shown in FIG. 9 can be mapped for the breakdown voltage, the tree showing the calculated BDV values with an error rate of less than 10% regarding the BDV value. Thus, the ascertainment according to the disclosure is superior even to the results from the method according to IEC 60243-1 performed using standard BDV lab equipment, said method having an error rate of up to 20%.

That is, the breakdown voltage can be calculated very well by means of the method and of the device according to the disclosure and can thus be determined with sufficient precision. In FIG. 9, the upper number in the field, e.g. 66.3, is the BDV value in [kV], and the lower number is the corresponding number of samples, n=3865. The rules, e.g. $W_C$>=9.5 [ppm], show the conditions of decision for transitioning to the next stage in the decision hierarchy. Units in FIG. 9 are BDV [kV], $W_C$ [ppm], TAN [mg/kg; KOH].

FIG. 10 shows a 2-dimensional function composed of the total acid number (TAN in mg/kg; KOH) and of the water content ($W_C$ in ppm) of multiple tested transformer oil samples. In FIG. 10, the most interesting $W_C$/TAN range, in which nearly 75% of all tested samples accumulated, is shown in particular.

FIG. 11 illustrates the spectral density function, which shows the different behavior of an aluminum-coated piezoelectric resonator in contact with the transformer oil. The oscillation range is between 75 kHz and 750 kHz. This impedance curve shows five clear areas which are taken into account when calculating the acoustic disbalance (AcDis).

FIG. 12 shows a polynomial approximation for BDV based on the measured lab and sensor data relating to breakdown voltage (BDV), water content ($W_C$), temperature (TEMP), relative saturation (RS), total acid number (TAN), interfacial tension (IFT) and acoustic disbalance (AcDis) of all lab samples, the BDV data having been standardized first and applied as exponents to an adjusted MATLAB™ regression function in order to arrive at an empirically ascertained model of the BDV based on specific $W_C$ and AcDis values. The residual error in FIG. 12 is in the margin of 2.5%.

According to the disclosure, the $W_C$ data were calculated from TEMP and RS data according to Formula (6). This resulted in the following matrix (7) for BDV calculation:

$$BDV(W_C, \text{AcDis}) = bi(W^T \cdot Q \cdot A)$$

wherein
$W=[1, W_C, W_C^2, W_C^3]^T$, and
$A=[1, \text{AcDis}, \text{AcDis}^2, \text{AcDis}^3]^T$ or $$BDV(W_C, AcDis) = \ln\left(\sum_{0 \leq p,q \leq 3} Q_{p,q} \cdot Wc^p \cdot AcDis^q\right)$$

and $$Q = \begin{bmatrix} -774.719 & 13668.212 & -62493.001 & 91578.430 \\ 3463.366 & -58357.859 & 263056.913 & -382222.994 \\ -5099.993 & 82366.071 & -366206.210 & 528174.797 \\ 2461.998 & -38292.458 & 168221.373 & -241289.917 \end{bmatrix}$$

It is obvious that figures of this kind can easily be processed by a 32-bit embedded system with a floating point unit (FPU). To avoid problems with difficult and very time-consuming matrix calculations, for which an embedded unit is not ideally suitable, and with the marginal stability of the presented model, a lookup table was created for this solution. It was found that a lookup table is a very adequate representation of the matrix solution and additionally comprises the marginal behavior of the transformer oil samples. Hence, a lookup table is the first choice regarding speed, resolution and stability. In conclusion, it should be noted that the calculation of the breakdown voltage (BDV) has a total residual error of less than 3.71%, which is an exceptional value.

REFERENCE SIGNS 100 stick
110 sensor portion
111 protective cover
112 resonance chamber
113 acoustic converter
114 moisture and/or temperature sensor
115 electronics
116 capacitor plates
117 retaining element
120 attachment portion
150 housing
151 spacer ring
152 insulating element
153 cable connector
200 measuring chamber
210 sensor portion
211 density and/or viscosity sensor
212 optical sensor
213 acoustic sensor
214 moisture and/or temperature sensor
215 capacitor plates
216 dielectric sensor
217 retaining element
250 housing
251 cable bushing

The invention claimed is:

1. A method for determining and/or monitoring the breakdown voltage of a transformer oil, comprising the steps of
   a) performing an acoustic impedance measurement of the transformer oil, the impedance of a medium partially or entirely disposed in the transformer oil and capable of naturally vibrating and/or transmitting vibrations to the transformer oil being determined in at least one frequency band of defined frequency width; and
   b) calculating a resonator quality factor for the frequency band based on the determination performed in step a); and
   c) calculating an acoustic disbalance of the transformer oil based on the calculation performed in step b); and
   d) ascertaining the breakdown voltage of the transformer oil based on the calculation performed in step c).

2. The method according to claim 1,
   wherein the method comprises an additional step c1) after step c):
   c1) registering at least one value of at least one characteristic physical property of the transformer oil.

3. The method according to claim 2,
   wherein at least one value of the temperature of the transformer oil is registered in step c1).

4. The method according to claim 2,
   wherein the method comprises an additional step c2) after step c1):
   c2) calculating the water content and/or the relative saturation in the transformer oil.

5. The method according to claim 1,
   wherein, in step a), the impedance is determined in four frequency bands each having a defined frequency width of 75 kHz.

6. The method according to claim 1,
   wherein the method additionally comprises the step of:
   e) displaying the ascertainment performed in step d).

7. A device for determining and/or monitoring the breakdown voltage of a transformer oil according to claim 1, comprising
   a) a first medium for performing an acoustic impedance measurement of the transformer oil, the impedance of the first medium, which is partially or entirely disposed in the transformer oil and capable of naturally vibrating or transmitting vibrations to the transformer oil, is determined in at least one frequency band of defined frequency width; and
   b) at least one analyzing and/or evaluating unit for calculating a resonator quality factor for the frequency band, for calculating an acoustic disbalance of the transformer oil and for ascertaining the breakdown voltage of the transformer oil.

8. The device according to claim 7,
   wherein the device comprises a second medium for registering at least one value of at least one characteristic physical property of the transformer oil.

9. The device according to claim 7,
   wherein the device comprises an output unit for displaying the ascertainment performed by the analyzing and/or evaluating unit.

10. The device according to claim 1,
wherein the first medium, the second medium, the analyzing and/or evaluating unit and/or the output unit is disposed in one component.

11. The device according to claim 10, wherein the component is a measuring chamber, a stick and/or an adapter.

12. The device according to claim 7,
wherein the device comprises a heating device.

13. A device of high-voltage technology, comprising transformer oil and a means for connecting the device to the device according to claim 7, the connection being a direct connection.

14. The device of high-voltage technology of claim 13, wherein the device of high-voltage technology comprises a transformer, a capacitor, a Petersen coil and/or a switch.

* * * * *

UNITED STATES PATENT AND TRADEMARK OFFICE
CERTIFICATE OF CORRECTION

| | |
|---|---|
| PATENT NO. | : 10,962,520 B2 |
| APPLICATION NO. | : 16/331773 |
| DATED | : March 30, 2021 |
| INVENTOR(S) | : Matthias Wrobel |

Page 1 of 1

It is certified that error appears in the above-identified patent and that said Letters Patent is hereby corrected as shown below:

In the Specification

Column 12, Lines 23-24, "electrical and/or to electromagnetic" should be -- electrical and/or electromagnetic --.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*